(12) United States Patent
Cajan et al.

(10) Patent No.: US 8,349,296 B2
(45) Date of Patent: Jan. 8, 2013

(54) AEROSOL FOAM COMPOSITION

(75) Inventors: Christine Cajan, Bad Ems (DE); Jutta Klutzny, Darmstadt (DE)

(73) Assignee: KPSS-KAO Professional Salon Services GmbH, Darmstadt (DE)

(*) Notice: Subject to any disclaimer, the term of this patent is extended or adjusted under 35 U.S.C. 154(b) by 1249 days.

(21) Appl. No.: 11/614,399

(22) Filed: Dec. 21, 2006

(65) Prior Publication Data

US 2008/0152610 A1 Jun. 26, 2008

(51) Int. Cl.
| | |
|---|---|
| *A61K 8/00* | (2006.01) |
| *A61K 8/02* | (2006.01) |
| *A61K 8/30* | (2006.01) |
| *A61K 9/12* | (2006.01) |
| *A61Q 5/00* | (2006.01) |
| *A61Q 5/04* | (2006.01) |
| *A61Q 5/06* | (2006.01) |

(52) U.S. Cl. ....... 424/45; 424/70.1; 424/70.4; 424/70.9; 424/70.11; 424/70.19; 424/70.22; 424/401; 424/DIG. 1

(58) Field of Classification Search ............. 424/45, 424/401, 70.1, 70.4, 70.9, 70.11, 70.19, 70.22, 424/DIG. 1
See application file for complete search history.

(56) References Cited

U.S. PATENT DOCUMENTS

| | | | | |
|---|---|---|---|---|
| 5,447,538 A | * | 9/1995 | Rosenbaum et al. | 8/405 |
| 5,858,343 A | * | 1/1999 | Szymczak | 424/73 |
| 6,383,993 B1 | * | 5/2002 | Maurin et al. | 510/119 |
| 2005/0169866 A1 | * | 8/2005 | Hannich et al. | 424/70.11 |
| 2005/0175563 A1 | * | 8/2005 | McNamara et al. | 424/70.1 |
| 2007/0202069 A1 | * | 8/2007 | Tamareselvy et al. | 424/70.12 |
| 2011/0008267 A1 | * | 1/2011 | Arkin et al. | 424/43 |

FOREIGN PATENT DOCUMENTS

| | | |
|---|---|---|
| EP | 0 576 748 A | 1/1994 |
| GB | 1 033 299 A | 6/1966 |
| WO | 00 57846 A | 10/2000 |

OTHER PUBLICATIONS

Merriam Webster's Collegiate Dictionary, 10th edition, Merriam-Webster, Inc.: Springfield, Massachusetts, 1996, pp. 1113-1114.*

* cited by examiner

*Primary Examiner* — James H. Alstrum-Acevedo
(74) *Attorney, Agent, or Firm* — Norris McLaughlin & Marcus PA

(57) ABSTRACT

The present invention relates to aerosol foam composition for styling and conditioning keratin fibres especially human hair. The composition improves hair styling with excellent hold and especially conditions hair with excellent shine, combability, volume and body and also excellent elasticity. The inventors of the present invention have found out surprisingly that an aqueous composition based on at least one hair styling polymer selected from anionic, non-ionic, cationic and/or amphoteric or zwitterionic ones which additionally comprises at least one oil or oily compound, at least one fatty acid soap, at least one emulsifier and at least one propellant shows excellent styling and conditioning benefits and has an appearance like a whipped cream which has not been known in the cosmetic market prior to the present invention.

11 Claims, No Drawings

AEROSOL FOAM COMPOSITION

The present invention relates to aerosol foam for styling and conditioning keratin fibres especially human hair. The composition improves hair styling with excellent hold and especially conditions hair with excellent shine, combability, volume and body and also excellent elasticity.

Styling compositions have been known for decades. They are used after usual hair cleansing and conditioning cycle to give hair better and long lasting hold, to improve hair volume or simply to fix the hair.

Styling and conditioning products comprising oil, oily substances and/or waxes have been known in the state of the art and have also been used widely. These products have been formulated generally as pastes and therefore, their applications bring difficulties in application on hair such as even distribution, optimal dosage etc.

Various types of formulations are found on hair care market such as spray, aerosol spray, paste, gel, foam or aerosol foam. Styling foams are easy to apply compared to a styling wax. Although the state of the art is quite advanced there are still needs for improvements from the application and also from the styling and conditioning properties of hair.

The objective of the present invention is to find out an aerosol foam wax composition with superior effects in terms of hair styling and conditioning and has at the same time unusual foam appearance.

The inventors of the present invention have found out surprisingly that an aqueous composition based on at least one hair styling polymer selected from anionic, non-ionic, cationic and/or amphoteric or zwitterionic ones which additionally comprises at least one oil or oily compound, at least one fatty acid soap, at least one emulsifier and at least one propellant shows excellent styling and conditioning benefits and has an appearance like a whipped cream which has not been know in cosmetic market prior to present invention.

Thus, the first objective of the present invention is an aqueous aerosol foam composition for keratin fibres especially for hair comprising at least one hair styling polymer selected from anionic, non-ionic, cationic and/or amphoteric or zwitterionic ones, at least one oil or oily compound, at least one fatty acid soap, at least one emulsifier and at least one propellant.

The second objective of the present invention is the use of an aqueous aerosol foam composition for keratin fibres especially for hair comprising at least one hair styling polymer selected from anionic, non-ionic, cationic and/or amphoteric or zwitterionic ones, at least one oil or oily compound, at least one fatty acid soap, at least one emulsifier and at least one propellant for styling and conditioning hair.

The compositions of the present invention comprise at least one hair styling polymer selected from the anionic, non-ionic, cationic and/or amphoteric or zwitterionic ones.

Suitable non-ionic polymer is first of all vinylpyrrolidon polymers either homopolymers or copolymers with, especially, vinylacetate. Those are known with the trade name "Luviskol" as homopolymers Luviskol K 30, K 60 or K 90 as well copolymers Luviskol VA 55, VA 64 from BASF AG.

Natural non-ionic polymers are as well suitable for the composition of the present invention. Those are such as cellulose, chitosan, guar gum and their derivatives.

As amphoteric polymers are copolymers of N-octyl acrylamide, (meth)acrylic acid and tert.-butyl aminoethyl methacrylate of the type "Amphomer®"; co-polymers from methacryloyl ethyl betaine and alkyl methacrylates of the type "Yukaformer®", e.g. the butyl methacrylate copolymer "Yukaformer® Am75"; copolymers from monomers containing carboxyl groups and sulfonic groups, e.g. (meth)acrylic acid and itaconic acid, with monomers such as mono- or dialkyl aminoalkyl(meth) acrylates or mono- or dialkyl aminoalkyl(meth)-acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199.

Suitable anionic polymers are vinyl alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/crotonic acid copolymers of the type "Resyn®"; sodium acrylate/vinyl alcohol copolymers of the type "Hydagen® F", sodium polystyrene sulfonate, e.g. "Flexan® 130"; ethyl acrylate/acrylic acid/N-tert.-butyl acrylamide copolymers of the type "Ultrahold®"; vinyl pyrrolidone/vinyl acetate/itaconic acid copolymers, acrylic acid/acrylamide copolymers or the sodium salts thereof.

Suitable cationic hair styling polymers are cationic cellulose type polymers know as Polymer JR type from Amerchol such as Polyquaternium 10 or cationic guar gum known with trade name Jaguar from Rhone-Poulenc and chemically for example Guar hydroxypropyl trimonium chloride. Furthermore, chitosan and chitin can also be included in the compositions as cationic natural polymers.

Furthermore, those cationic polymers known with their CTFA category name Polyquaternium may as well be added into the compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46.

As well those polymers known with their CTFA category name Quaternium can as well be suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7, It is also possible to use mixtures of various cationic polymers.

The cationic polymers also include the quaternized products of graft polymers from organopolysiloxanes and polyethyl oxazolines described in EP-A 524 612 and EP-A 640 643. Among these especially preferred is the compound know with the INCI name Polysilicone-9.

Concentration of polymers of anionic, cationic, non-ionic and/or amphoteric or zwitterionic character is in the range of 0.5-20%, preferably 2-15% and more preferably 3-12% and most preferably 4-10% by weight, calculated to the total composition excluding propellant.

Aerosol foam composition of the present invention comprises at least one oil or oily compound at a concentration of 1 to 35%, preferably 2 to 30% more preferably 3 to 30% and most preferably 5 to 25% by weight calculated to total composition excluding propellant.

Suitable oil or oily ingredients are those of natural oils such as olive oil, avocado oil, coconut oil, palm oil, sesame oil, peanut oil, whale oil, sunflower oil, almond oil, peach kernel oil, wheat germ oil, macadamia nut oil, night primrose oil, jojoba oil, castor oil, soya oil, and the derivatives thereof. Mineral oils such as paraffin oil and petrolatum are suitably contained within the scope of the present invention, The compositions according to the present invention may comprise one or more silicone oils as the oily compound. Preferred silicone oils are known with their INCI name as dimethicone, dimethiconol, cyclomethicone and phenyltrimethicone. Commercially, they are available from various companies for example Dow Corning with the known DC series, Wacker Chemie and Toray silicones. All commercially available silicones are suitable in the compositions of the present invention. Examples to those are DC 200 series, DC1401, DC 1403, DC 1501 and DC 1503.

Further, suitable oil components are in particular fatty alcohol fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters, cetyl palmitate, etc.

Further suitable ones are fatty alcohol ethoxylates with a saturated or unsaturated, branched or linear alkyl chain with 12 to 24 C atoms and with ethoxylation degree of up to 10 ethyoxy units, preferably 8 ethoxy units. Examples are Ceteareth-2, Ceteareth-3, Ceteth-1, Ceteth-2, Ceteth-3, Myreth-2, Myreth-3, Oleth-2 and Oleth-3.

It should as well be noted that hair treatment compositions can contain mixture of one or more oil or oily compounds as listed above.

The composition of the present invention comprises at least one fatty acid soap. The fatty acids suitable are saturated or unsaturated, branched or linear with 10 to 24 C atoms, preferably 12 to 22 C atoms. The most preferred are palmitic and stearic acids saponified with sodium and/or potassium hydroxide. Concentration of fatty acids is in the range of 0.1 to 7.5%, preferably 0.2 to 5%, more preferably 0.25 to 3% and most preferably 0.5 to 3% by weight calculated to total composition excluding propellant.

Composition of the present invention comprises at least one emulsifier selected from anionic, non-ionic, cationic and amphoteric surfactants. The most preferred emulsifiers are non-ionic ones. Concentration of at least one emulsifier is in the range of 0.2 to 15%, preferably 0.5 to 10% and more preferably 0.5 to 7.5% by weigh calculated to total composition excluding propellant.

Suitable non-ionic emulsifiers are first of all fatty alcohol ethoxylates with at least 10, preferably 15 and more preferably 20 ethoxy units. Nonlimiting examples to those are oleth-10, oleth-11, oleth-12, oleth-15, oleth-16, oleth-20, oleth-25, oleth-30, oleth-35, oleth-40, laureth-10, laureth-11, laureth-12, laureth-13, laureth-15, laureth-16, laureth-20, laureth-25, laureth-30, laureth-35, laureth-40, laureth-50, ceteth-10, ceteth-12, ceteth-14, ceteth-15, ceteth-16, ceteth-17, ceteth-20, ceteth-25, ceteth-30, ceteth-40, ceteth-45, cetoleth-10, cetoleth-12, cetoleth-14, cetoleth-15, cetoleth-16, cetoleth-17, cetoleth-20, cetoleth-25, cetoleth-30, cetoleth-40, cetoleth-45, ceteareth-10, ceteareth-12, ceteareth-14, ceteareth-15, ceteareth-16, ceteareth-18, ceteareth-20, ceteareth-22, ceteareth-25, ceteareth-30, ceteareth-40, ceteareth-45, ceteareth-50, isosteareth-10, isosteareth-12, isosteareth-15, isosteareth-20, isosteareth-22, isosteareth-25, isosteareth-50, steareth-10, steareth-11, steareth-14, steareth-15, steareth-16, steareth-20, steareth-25, steareth-30, steareth-40, steareth-50, steareth-80 and steareth-100. Additional examples of similar compounds can be found in the cosmetic ingredient dictionaries and cosmetic textbooks.

Further non-ionic emulsifiers within the meaning of the present invention are polyalkyleneglycol ether of fatty acid glyceride or partial glyceride with at least 30 polyalkylene units are with 30 to 1000, preferably 30 to 500, more preferably 30 to 200 and most preferably 40 to 100 polyethyleneglycol units. Examples to those are PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil, PEG-100 castor oil, PEG-200 castor oil. Additional examples of similar compounds can be found in the cosmetic ingredient dictionaries and cosmetic textbooks.

Further suitable non-ionic emulsifiers are monoglycerides such as glyceryl stearate, glyceryl palmitate, glyceryl myristate, glyceryl behenate.

The suitable anionic surfactants as emulsifiers are those customarily used in cleansing compositions such as ethoxylated fatty alcoholos sulfates, carboxylates. Nonlimiting examples to those are sodium laureth sulfate and sodium laureth carboxylate. Another anionic surfactant suitable is trilaureth-4 phosphate.

Amphoteric surfactants are also the ones customarily used in cleansing compositions. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

The cationic surfactants useful in the compositions are according to the general formula below:

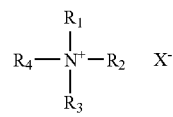

where $R_1$ is a saturated or unsaturated, branched or linear alkyl chain with 8-22 C atoms or

where $R_5$ is saturated or unsaturated, branched or linear alkyl chain with 7-21 C atoms and n has typical value of 0-4 or

where $R_6$ is saturated or unsaturated, branched or linear alkyl chain with 7-21 C atoms and n has typical value of 0-4, and $R_2$ is a hydrogen, lower alkyl chain with 1 to 4 carbon atoms, saturated or unsaturated, branched or linear alkyl chain with 8-22 C atoms or

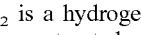

where $R_5$ is saturated or unsaturated, branched or linear alkyl chain with 7-21 C atoms and n has typical value of 0-4 or

where $R_6$ is saturated or unsaturated, branched or linear alkyl chain with 7-21 C atoms and n has typical value of 0-4, and $R_3$ and $R_4$ are independent from each other H or lower alkyl chain with 1 to 4 carbon atoms, and X is chloride, bromide or methosulfate.

It should be noted that quaternary ammonium compounds with single alkyl, alkoyl, alkylamido chains are preferred as emulsifiers within the meaning of the present invention. The ones with two alkyl, alkoyl or alkylamido chains are used to improve hair conditioning properties. Suitable cationic surfactants and or conditioning agents are, for example, long-chain quaternary ammonium compounds which can be used alone or in admixture with each other, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride and dioleoylethyl dimethyl ammonium methosulfate, etc.

From the above quaternary ammonium compounds disclosed with the general formula, suitable ones are those compounds known per se and are on the market, for example, under the trade names "Schercoquat®", "Dehyquart®" and "Tetranyl®". Use of these compounds, the so-called "ester-quats", in hair care compositions is described, for example, in WO-A 93/107 48, WO-A 92/068 99 and WO-A 94/166 77, wherein, however, there is no reference made to the combinations according to the present invention and the advantageous properties thereof.

Again from the above quaternary ammonium compounds disclosed with the general formula, suitable ones are these compounds are known per se and on the market, for example, under the trade name "INCROQUAT® HO" or "OCS". Those compounds are known with a general ingredient category under "amidoquat" in the cosmetic industry.

The compositions of the present invention comprise at least one propellant at a concentration of 2 to 40%, preferably 5 to 35%, more preferably 10 to 30% by weight, calculated to the total aerosol foam composition. Useful propellants are, for example, hydrocarbons such as propane, n-butane, n-butane and the mixtures thereof, haloalkanes, dimethyl ether, carbon dioxide and/or nitrogen or their mixtures. The pressure in the aerosol container preferably ranges from about 1.5 to 6 bar.

The most preferred propellant is dimethyl ether. It is further preferred that the propellant is mixture of 2 propellants preferably mixture or dimethyl ether and hydrocarbons such as propane, n-butane, n-butane and their mixtures at a weight ratio of 5:1 to 1:5, preferably 3:1 to 1:3 and more preferably 3:1 to 1:1.

The compositions of the present invention can contain one or more organic solvents within the scope of the invention, Suitable ones are ethanol, propanol, isopropanol, isopentane, n-pentane, n.hexane, dimethoxymethane, benzyl alcohol, benzyloxyethanol, alkylene carbonates such as ethylene carbonate and propylene carbonate, phenoxyethanol, butanol, isobutanol, cyclohexane, cyclohexanol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. The most preferred organic solvents are ethanol, isopropanol and propanol without limiting the scope. Concentration of solvents is up to 40%, preferably 5 to 35% and most preferably 10 to 30% by weight calculated to total composition excluding propellant.

In a preferred embodiment of the present invention, compositions comprise at least one organic solvent, preferably ethanol or ethanol in mixture with isopropanol at a concentration of up to 40%, more preferably 5 to 35% and most preferably 10 to 30% by weight calculated to total composition excluding propellant.

The composition of the present invention can comprise polyols at a concentration of 0.5 to 15%, preferably 1 to 10%, more preferably 2 to 5% by weight calculated to the total concentration excluding propellant. The most preferred ones are glycerine, propylene glycols, butylene glycol and hexylene glycol.

Cationic silicones know with INCI name as amodimethicone can as well be contained in the compositions of the present invention. Commercially it is available under the trade name DC 949 in emulsified form in mixture with a nonionic surfactant and a cationic surfactant.

The compositions according to the invention may also comprise further agents, such as proteins, for example bamboo protein, and protein hydrolyzates and polypeptides, e.g. keratin hydrolyzates, collagen hydrolyzates of the type "Nutrilan®" or elastin hydrolyzates, as well as, in particular vegetable, optionally cationized protein hydrolyzates, for example "Gluadin®".

Additional natural plant extracts can as well form part of the compositions of the present invention. Those are incorporated usually in an amount of about 0.01% to about 5%, preferably 0.05% to 3.5%, in particular 0.1% to 2% by weight, calculated as dry residue thereof to the total composition excluding propellant. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis". $4^{th}$ Ed.

Compositions of the present invention may contain UV filters either for stabilization of the product colour and/or for protection of hair from environmental influences such as loss of elasticity, loss of hair colour (bleaching effect of sun light). Suitable UV-absorbing substance are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher.

The suitable amount of the UV-absorber ranges from about 0.01% to 1% by weight, calculated to the total composition excluding propellant. Attention should be paid to the stability and solubility especially when using UV filter as salts, e.g. anionic UV filter salts.

pH of the compositions measured before confectioning as aerosol product vary between 4 to 9, preferably 5 to 8 and more preferably 5.5 to 8 measured 25° C.

It has further been observed that when the composition comprise further at least one polyethylenglycol with a molecular weight of above 10,000, the foam as taken out from the aerosol can forms stringy appearance when touched and extended by hand or fingers. Therefore, it is further object of the present invention that the compositions additionally comprise at least one polyethyleneglycol with molecular weight of above 10,000. Those are known with their CTFA name for example PEG-30M. which has a molecular weight of 30.000 and commercially available from the company Amerchol under the trade name Polyox WSR. for example Polyox WSR N60-K. which has a CTFA adopted name PEG-45M. polyethyleneglycol with 45.000 molecular weight. Further examples are such as PEG-14M, PEG-20M, PEG-23M, PEG-25M, PEG-90M, PEG-115M, PEG-160M, etc.

Concentration of the high molecular weight polyethyleneglycol, one or mixture of more than one, is in the range of 0.05% to 2.5%, preferably 0.1% to 1.5% and most preferably between 0.1 to 1.0% by weight calculated to total composition excluding propellant.

Compositions of the present invention may further comprise any compound needed for the application purposes and at the same time allowed for using in cosmetic products such as ceramides, sphingolipids, moisturizing agents, preservatives, chelating agents, radical scavengers, antioxidants, fragrance, dyestuffs and pH regulators.

According to the invention, aerosol foam composition may comprise dyestuffs either for colouring the product or for hair dyeing purpose. For product colouring anionic dyes are preferred.

Anionic dyes suitable are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Suitable cationic dyestuffs are in principal those available on the market for hair colouring applications. Some examples to those are: Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51 Basic Red 76, Basic Violet 1, Basic Violet 2, Basic Violet 3, Basic Violet 10, Basic Violet 14 and Basic Yellow 57, Basic Orange 31 and Basic Yellow 87. For this purpose, special reference is made to the PCT application WO 95/15144 of Ciba-Geigy AG. All cationic dyes disclosed therein are included here by reference.

Additionally, neutral dyes (HC dyes), so called nitro dyes either alone or in addition to the cationic and/or anionic direct dyes may be used in the compositions of the present invention. Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of the dyes is very much dependent on the purpose. For product dyeing purposes very low concentration such as up to 0.01% by weight, calculated to total composition excluding propellant. However for hair colouring purpose higher concentrations is required. Typically the concentration range is from 0.01 to 1% by weight calculated to total composition excluding propellant.

Further objective of the present invention is process for conditioning and styling keratin fibres especially hair wherein a composition comprising at least one hair styling polymer selected from anionic, non-ionic, cationic and/or amphoteric or zwitterionic ones, at least one oil or oily compound, at least one fatty acid soap, at least one emulsifier and at least one propellant is applied onto wet hair and distributed homogeneously on the hair and subsequently dried.

Still further objective of the present invention is process for conditioning and styling keratin fibres especially hair wherein a composition comprising at least one hair styling polymer selected from anionic, non-ionic, cationic and/or amphoteric or zwitterionic ones, at least one oil or oily compound, at least one fatty acid soap, at least one emulsifier and at least one propellant is applied onto dry hair and distributed homogeneously on the hair.

The following examples are to illustrate the invention and non-limiting.

EXAMPLE 1

|  | % by weight |
|---|---|
| Petrolatum | 10 |
| Stearic acid | 1 |
| Olive oil | 3 |
| Potassium hydroxide | q.s. pH 7.0 |
| Ceteareth-20 | 1 |
| VP/VA Copolymer | 10 |
| PEG-40 Hydrogenated castor oil | 0.2 |
| Cetrimonium chloride | 0.2 |
| Fragrance | q.s. |
| Water | q.s. to 100 |

The above composition was produced as follows: Petrolatum, stearic acid, olive oil and ceteareth-20 were mixed and melted in a vessel at approximately 80° C. and potassium hydroxide as dissolved in water was added and mixed for approximately 30 min. Subsequently the batch was cooled down to approximately 40° C. and mixed with aqueous solution of VP/VA Copolymer and cetrimonium chloride. Finally fragrance PEG-40 Hydrogenated castor oil mixture was added and mixed until homogeneity. pH was measured at 20° C. Generally in the case that pH differs from the target value it can be adjusted by adding aqueous solution of potassium hydroxide.

The above composition is filled into an aerosol can with 80% by weight bulk and 20% by weight of dimethylether, both concentrations are calculated to total product including propellant.

Hair treated with the above composition, applied onto dry hair, is easy and quick to style, has intensive shine, and excellent hold and also shows excellent elasticity.

For comparative purposes the above composition was produced without stearic acid. The amount was simply replaced with water. First of all, the foam produced had a different appearance in terms of compactness and bubble size. Foam obtained with the inventive compositions was with fine bubbles and more compact as evaluated by hair dressers. Furthermore the comparative composition was compared with the Example 1 in a half side test with 10 female volunteers having around shoulder length hair. The hair was first washed with a commercially available shampoo under the brand name Goldwell and subsequently around 3 g of foam was applied to each side which was followed by wet and dry, after drying with a hair dryer, evaluation by hair dressers. Finally, the volunteers were asked for their preference. The results are summarized in the Table I.

TABLE I

Results of half side comparative test

|  | Example 1 | Comparative example | No difference |
|---|---|---|---|
| Easy to work into hair | 6 | 2 | 2 |
| Setting effect | 7 | 1 | 2 |
| Oilyness | 1 | 7 | 2 |
| Shine | 8 | 0 | 2 |
| Natural fell | 8 | 1 | 1 |
| Preference | 9 | 1 | 0 |

From the above results it is clear that presence of fatty acid soap improves application, and effects on hair.

Afterwards the hair was shampooed again only for once with the same shampoo used before the application of styling foams and washability was judged again by hair dressers. It was reported that in all case the inventive composition was found to be washed out from the hair without leaving any rest. For comparative composition, on the other hand, in 60% of the cases the remains were reported.

Very similar results were obtained when the test was carried out when the compositions were applied on dry hair.

EXAMPLE 2

|  | % by weight |
|---|---|
| Ceteareth-3 | 12 |
| Stearic acid | 1.5 |
| Palmitic acid | 1.5 |
| Mineral oil | 8 |
| Potassium hydroxide/Sodium hydroxide (1:1 mixture by weight) | q.s. to pH 6.5 |
| Glycerylstearate/PEG 100 stearate | 2. |
| Acrylates/octylacrylamide copolymer | 6 |
| Propylene glycol | 2 |
| PEG-60 Hydrogenated castor oil | 0.2 |
| PEG-90M | 0.2 |
| Panthenol | 2 |
| Fragrance, preservative | q.s |
| Water | q.s to 100 |

The above composition was produced in a similar way as in Example 1.

The above composition is filled into an aerosol can with 80% by weight bulk and 20% by weight of propellant which is mixture of dimethylether and propane/butane mixture at a weight ratio of 1:3, both concentrations are calculated to total product including propellant.

Hair treated with the above composition, applied onto dry hair, is easy and quick to style, has intensive shine, and excellent hold and also shows excellent elasticity. A curly hair treated with the above compositions showed excellent curl appearance and bounce.

EXAMPLE 3

|  | % by weight |
|---|---|
| Ceteareth-3 | 12 |
| Palmitic acid | 3 |
| Isopropyl palmitate | 8 |
| Potassium hydroxide | q.s. to pH 7.5 |
| Oleth-20 | 2 |
| Vinylcaprolactam/VP/dimethylaminoethyl Methacrylate | 2 |
| Polyquaternium-16 | 1 |
| Propylene glycol | 2 |
| PEG-60 Hydrogenated castor oil | 0.2 |
| Benzophenone-4 | 0.2 |
| Basic red 51 | 0.02 |
| Fragrance, preservative | q.s |
| Water | q.s to 100 |

The above composition was produced in a similar way as in Example 1.

The above composition is filled into an aerosol can with 85% by weight bulk and 15% by weight of propellant which is mixture of propane/butane mixture and 152a at a weight ratio of 1:1.5, both concentrations are calculated to total product including propellant.

Hair treated with the above composition, applied onto dry hair, is easy and quick to style, has intensive shine, and excellent hold and also shows excellent elasticity. Additionally because of the presence of cationic red dyestuff, slight red reflection on hair was observed.

EXAMPLE 4

|  | % by weight |
|---|---|
| Petrolatum | 10 |
| Stearic acid | 2.5 |
| Dimethicone | 5 |
| Potassium hydroxide | q.s. pH 7.0 |
| Trilaureth-4 phosphate | 5 |

-continued

|  | % by weight |
| --- | --- |
| PVP | 5 |
| Propylene glycol | 2 |
| PEG-45M | 0.5 |
| PEG-60 Hydrogenated castor oil | 0.2 |
| Octylmethoxycinnamate | 0.2 |
| CI 15985 | 0.005 |
| Fragrance, preservative | q.s |
| Water | q.s to 100 |

The above composition was produced in a similar way as in Example 1.

The above composition is filled into an aerosol can with 75% by weight bulk and 24% by weight of propane/butane mixture as a propellant and 1% by weight of n-pentane, all concentrations are calculated to total product including propellant.

EXAMPLE 5

|  | % by weight |
| --- | --- |
| Petrolatum | 10 |
| Stearic acid | 2.5 |
| Dimethicome | 5 |
| Potassium hydroxide | q.s. pH 7.0 |
| Trilaureth-4 phosphate | 5 |
| PVP | 5 |
| Propylene glycol | 2 |
| PEG-45M | 0.5 |
| PEG-60 Hydrogenated castor oil | 0.2 |
| Octylmethoxycinnamate | 0.2 |
| CI 15985 | 0.005 |
| Fragrance, preservative | q.s |
| Water | q.s to 100 |

The above composition was produced in a similar way as in Example 1.

The above composition is filled into an aerosol can with 75% by weight bulk and 24% by weight of propane/butane mixture as a propellant and 1% by weight of methylal (dimethoxymethane), all concentrations are calculated to total product including propellant.

The invention claimed is:

1. An aqueous aerosol foam composition for keratin fibres comprising 3 to 20 wt. % of at least one hair styling polymer selected from anionic, non-ionic, cationic and/or amphoteric or zwitterionic polymers, at least one oil or oily compound, 0.1 to 3 wt. % of at least one fatty acid soap, 0.2 to 7.5 wt. % of at least one emulsifier and 10 to 40% of at least one propellant selected from the group consisting of hydrocarbons, haloalkanes and dimethyl ether, wherein the concentrations of hair styling polymer, fatty acid soap and emulsifier are calculated to a total concentration excluding propellant.

2. An aqueous aerosol foam composition according to claim 1 comprising at least one oil or oily compound at a concentration of 1 to 35% by weight calculated to total composition excluding propellant.

3. An aqueous aerosol foam composition according to claim 2 wherein at least one oil or oily compound is selected from the group consisting of natural oils, mineral oil, silicone oils, fatty alcohols, fatty acid esters, fatty alcohol ethoxylates with saturated or unsaturated branched or linear alkyl chain with 12 to 24 C atoms, and mixtures thereof.

4. An aqueous aerosol foam composition according to claim 1 wherein the fatty acid soap is selected from the group consisting of palmitic and stearic acids saponified with sodium hydroxide or potassium hydroxide.

5. An aqueous aerosol foam composition according to claim 1 comprising a mixture of 2 propellants.

6. An aqueous aerosol foam composition according to claim 5 wherein the propellant mixture comprises dimethylether and hydrocarbons at a weight ratio of 5:1 to 1:5.

7. An aqueous aerosol foam composition according to claim 1 comprising at least one UV filter.

8. An aqueous aerosol foam composition according to claim 1 further comprising at least one polyethyleneglycol with a molecular weight of above 10,000.

9. An aqueous aerosol foam composition according to claim 1, comprising at least one direct dye.

10. An aqueous aerosol foam composition according to claim 1 comprising at least one organic solvent.

11. An aqueous aerosol foam composition according to claim 1 comprising between 1 to 3 wt. % of fatty acid soap, calculated to a total concentration excluding propellant.

* * * * *